United States Patent [19]

Barda

[11] Patent Number: 5,025,090

[45] Date of Patent: Jun. 18, 1991

[54] DECOLORIZATION OF DIHYDROXYDIPHENYL SULFONE

[75] Inventor: Henry J. Barda, Brunswick, N.J.

[73] Assignee: AKZO NV, Arnhem, Netherlands

[21] Appl. No.: 473,482

[22] Filed: Feb. 1, 1990

[51] Int. Cl.$^5$ .......................................... C07C 315/04
[52] U.S. Cl. ..................................................... 568/33
[58] Field of Search ........................................ 568/33

[56] References Cited

U.S. PATENT DOCUMENTS

| | | | |
|---|---|---|---|
| 2,752,398 | 6/1956 | Riley | 568/702 |
| 4,154,964 | 5/1979 | Balg | 568/757 |
| 4,696,774 | 9/1987 | Telschow | 562/826 |
| 4,822,916 | 4/1989 | Aaronson et al. | 568/28 |
| 4,933,494 | 6/1990 | Tubota et al. | 568/33 |

FOREIGN PATENT DOCUMENTS 2088857  6/1982  United Kingdom ................ 568/33

OTHER PUBLICATIONS

Derwent Abstract of Japanese Patent 58-206,551 published Dec. 1, 1983.
Derwent Abstract of Japanese Patent 57-35,559 published Feb. 26, 1982 and English translation.

*Primary Examiner*—Mary E. Ceperley
*Attorney, Agent, or Firm*—Richard P. Fennelly; Louis A. Morris

[57] ABSTRACT

Trivalent phosphorous compounds (e.g., phosphorous acid and dialkyl phosphites) if present in small amount during the reaction of phenol with a sulfonating agent or a phenol sulfonic acid yield a dihydroxydiphenyl sulfone product that is less colored.

9 Claims, No Drawings

DECOLORIZATION OF DIHYDROXYDIPHENYL SULFONE

BACKGROUND OF THE INVENTION

Dihydroxydiphenyl sulfone (hereinafter termed "DHS") is a known monomer used in the synthesis of polymers. For aesthetic reasons, it is important for the monomer to be as free of undesired color as possible since a colored monomer will impart an undesired color to the final polymer product.

Various disclosures exist in the prior art in regard to the use of inorganic phosphorus or organophosphorus compounds to achieve certain desired results with various chemicals.

U.S. Pat. No. 2,752,398 describes the use of phosphoric acid, a pentavalent phosphorus inorganic compound, to color stabilize phenols. More recently, U.S. Pat. No. 4,154,964 mentioned purification of a phenol compound prepared by the decarboxylation oxidation of a benzoic acid by countercurrent contact with phosphoric acid under certain temperature conditions.

Japanese Patent Publication No. 58 206,551 describes diaryl sulfone production by reaction of an aromatic halohydrocarbon with chlorosulfonic acid in the presence of phosphorus pentoxide, a pentavalent phosphorus compound.

Japanese Patent Publication No. 57 35,559 teaches dihydroxydiphenyl sulfone production by reaction of phenol with a sulfonating agent (e.g., sulfuric acid) or phenol sulfuric acid in the presence of a zinc, iron, magnesium, boron, and/or phosphorus compound. The disclosure of this reference in regard to what phosphorus compounds to use is also limited to pentavalent phosphorus compounds: phosphoric acid; the phosphates; the polyphosphoric acids; and the polyphosphates. These compounds are said to accelerate the reaction so that the product is formed in a short period of time and has a small content of impurities of by-products. They are used at 0.01% to 10% by weight of the reactants.

U.S. Pat. No. 4,822,916 to A. M. Aaronson et al. describes a process for preparing diaryl sulfones in which certain pentavalent phosphorus compounds (e.g., $PCl_5$, $POCl_3$, $POBr_3$, $P_2O_5$, etc.) can be used in stoichiometric amount as condensing agents during the second stage of the two stage reaction. That patent mentions at Col. 3, lines 3-10, that $P_2O_5$, a pentavalent phosphorus compound, reduces the amount of discoloration in the product.

SUMMARY OF THE INVENTION

It has been found, in accordance with the instant invention, that trivalent phosphorus compounds can be used to reduce the formation of colored dihydroxydiphenyl sulfone during its manufacture by the reaction of phenol with a sulfonating agent or phenol sulfonic acid.

DETAILED DESCRIPTION OF THE INVENTION

The general reaction process for forming dihydroxydiphenyl sulfone to which the instant invention relates involves the reaction of phenol with either a sulfonating agent (e.g., sulfuric acid) or phenol sulfonic acid, and it is well known to persons of ordinary skill in the art. Representative references which are illustrative of the various specific techniques which can be employed using the general phenol-sulfuric acid route, for example, include: U.S. Pat. Nos. 3,297,766; 3,318,956; 3,366,692; and 3,383,421, each of which is incorporated herein by reference.

The improvement to which the present invention relates is the use of an effective, substantially less than stoichiometric, amount, e.g., 0.1% to 5%, by weight of the combined amounts of reactants, of a trivalent phosphorus compound to result in a less colored dihydroxydiphenyl sulfone product. Representative compounds include those of the general formula where R can be —OAlkyl, —OAryl, —OH, or —Halogen with the respective R groups being the same or different. Included within this class of compounds are phosphorous acid and the dialkyl phosphites (e.g., dimethyl phosphite).

The instant invention will be further understood by the Examples which follow.

EXAMPLES 1–4

The apparatus consisted of a 250 ml four-neck flask provided with a stirrer containing a vapor tight bearing, a subsurface thermometer, an addition funnel and a fractionating column. The fractionating column had an inside diameter of 2.5 cm and had a silvered vacuum jacket. It was filled to a 28.5 cm height with 0.24 inch (6 mm) stainless steel protruded packing. Above the fractionating column was a vacuum jacketed Barrett moisture trap containing a thermometer immersed in the vapors. Above the Barrett trap was a condenser cooled by a circulating refrigerated bath which was set at 10° C. The stirrer was set at about 190 rpm. The flask was heated in a thermostated silicone oil bath.

The solvents were washed with concentrated sulfuric acid before use. The Barrett trap was filled with Isopar C solvent. To the flask was added 15.0 grams of Isopar C solvent, 120.0 grams of Isopar H solvent and phenol. In Examples 2 and 4, phosphorous acid and dimethyl phosphite, respectively, were also added. To the addition funnel was added 96.05% sulfuric acid. The content of the flask was then heated to 100° C., and the sulfuric acid added at 100°–110° C. followed by a hold period. The addition and hold period together took 20 minutes. The oil bath was then brought to 188°–191° C. and held at that temperature throughout the reaction. Reflux time, starting when vapors began to condense in the Barrett trap to the removal of the oil bath, was 7 hours. The aqueous phase was periodically drained from the Barrett trap so that it always contained from 1–2 ml. After the first 30–60 minutes of reflux the temperature in the reaction flask was 160°–170° C. The reaction mixture was then cooled to less than 90° C., most of the Isopar solvent replaced by water and stirred at 90° C. for 1–2 hours. After cooling to 30° C., the slurry was filtered, washed three times with water, and dried to constant weight.

A 2.0 grams sample of the dihydroxydiphenyl sulfone product was dissolved in acetone to make a 25 ml solution, and the absorbance measured at 420 nm, in a 1 cm cell with acetone in the reference cell.

The results below illustrate that positive results (a decrease in absorbance) was found for Examples 2 and 4 over their respective controls (Examples 1 and 3):

| Example No. | 1 | 2 | 3 | 4 |
| --- | --- | --- | --- | --- |
| Phenol, gm | 56.3 | 56.3 | — | — |

-continued

| Example No. | 1 | 2 | 3 | 4 |
|---|---|---|---|---|
| Phenol, gm | — | — | 112.6 | 112.6 |
| 96.05% sulfuric acid, gm | 26.4 | 26.4 | 52.8 | 52.8 |
| Phosphorous acid, gm | — | 0.3 | — | — |
| Dimethyl phosphite, ml | — | — | — | 0.7 |
| Absorbance | 0.117 | 0.065 | 0.693 | 0.249 |
| Decrease in absorbance, % | — | 44.4 | — | 64.1 |

The foregoing Examples have been presented for illustrative purposes only and should not therefore be construed in a limiting sense. The scope of protection sought is set forth in the claims which follow.

I claim:

1. A process for the production of a less colored dihydroxydiphenyl sulfone by reaction of phenol with a sulfonating agent or phenol sulfonic acid wherein the improvement comprises adding an effective amount of a trivalent phosphorus compound for color reduction during the reaction.

2. A process as claimed in claim 1 wherein the phosphorus compound has the formula $PR_3$ where R is selected from the group consisting of —OAlkyl, —OAryl, —OH, and —Halogen.

3. A process as claimed in claim 2 wherein the amount of phosphorus compound ranges from about 0.1% to about 5%, by weight of the reactants.

4. A process as claimed in claim 2 wherein the phosphorus compound is phosphorous acid.

5. A process as claimed in claim 3 wherein the phosphorus compound is phosphorous acid.

6. A process as claimed in claim 2 wherein the phosphorus compound is a dialkyl phosphite.

7. A process as claimed in claim 3 wherein the phosphorus compound is a dialkyl phosphite.

8. A process as claimed in claim 2 wherein the phosphorus compound is dimethyl phosphite.

9. A process as claimed in claim 3 wherein the phosphorus compound is dimethyl phosphite.

* * * * *